(12) United States Patent
Kent

(10) Patent No.: US 11,414,852 B2
(45) Date of Patent: Aug. 16, 2022

(54) REMOVABLE TRASH FILTER BASKET WITH HINGED WIER FOR CATCH BASINS

(71) Applicant: Bio Clean Environmental Services, Inc., Irving, TX (US)

(72) Inventor: Zachariha J. Kent, Fair Oaks Ranch, TX (US)

(73) Assignee: Bio Clean Environmental Services, Inc., Oceanside, CA (US)

( * ) Notice: Subject to any disclaimer, the term of this patent is extended or adjusted under 35 U.S.C. 154(b) by 0 days.

(21) Appl. No.: 17/027,654

(22) Filed: Sep. 21, 2020

(65) Prior Publication Data

US 2021/0087804 A1    Mar. 25, 2021

Related U.S. Application Data

(60) Provisional application No. 62/903,855, filed on Sep. 22, 2019.

(51) Int. Cl.
*E03F 5/04* (2006.01)
*E03F 5/046* (2006.01)

(52) U.S. Cl.
CPC ............ *E03F 5/0404* (2013.01); *E03F 5/046* (2013.01)

(58) Field of Classification Search
CPC ............ E03F 5/0404; E03F 5/046; E03F 5/14
USPC .......................... 210/163, 164, 170.03, 747.3
See application file for complete search history.

(56) References Cited

U.S. PATENT DOCUMENTS

| | | | | |
|---|---|---|---|---|
| 1,711,674 | A * | 5/1929 | Egan | E03F 5/046 210/163 |
| 3,127,821 | A * | 4/1964 | Lebaron, Jr. | E03F 5/06 210/163 |
| 5,820,762 | A * | 10/1998 | Bamer | E03F 5/0404 210/164 |
| 6,270,663 | B1 * | 8/2001 | Happel | E03F 5/0404 210/163 |
| 8,608,956 | B2 * | 12/2013 | Moulton | E03F 5/14 210/163 |
| 9,322,156 | B2 * | 4/2016 | McInnis | E03F 5/0404 |
| 2003/0132150 | A1 * | 7/2003 | Happel | E03F 5/046 210/163 |
| 2005/0183997 | A1 * | 8/2005 | Happel | E03F 5/0404 210/163 |
| 2005/0207839 | A1 * | 9/2005 | Tremouilhac | E03F 5/046 404/5 |
| 2011/0139694 | A1 * | 6/2011 | Mondschein | E03F 5/0404 210/163 |

FOREIGN PATENT DOCUMENTS

WO    WO 2009/014370    *   1/2009

* cited by examiner

*Primary Examiner* — Christopher Upton
(74) *Attorney, Agent, or Firm* — Steven W. Webb

(57) ABSTRACT

Preferred embodiments of the invention provide improved catch basin filter system for maintenance and access. Preferred embodiments are composed of a diversion trough, a hinged pivot weir, weir to trough mounting brackets, under mounts, weir stops, a weir trash screen, a hole in the weir bottom section and a filter basket, wherein: the assembly is affixed to the catch basin chamber wall directly below an above ground access point for ease of maintenance.

13 Claims, 10 Drawing Sheets

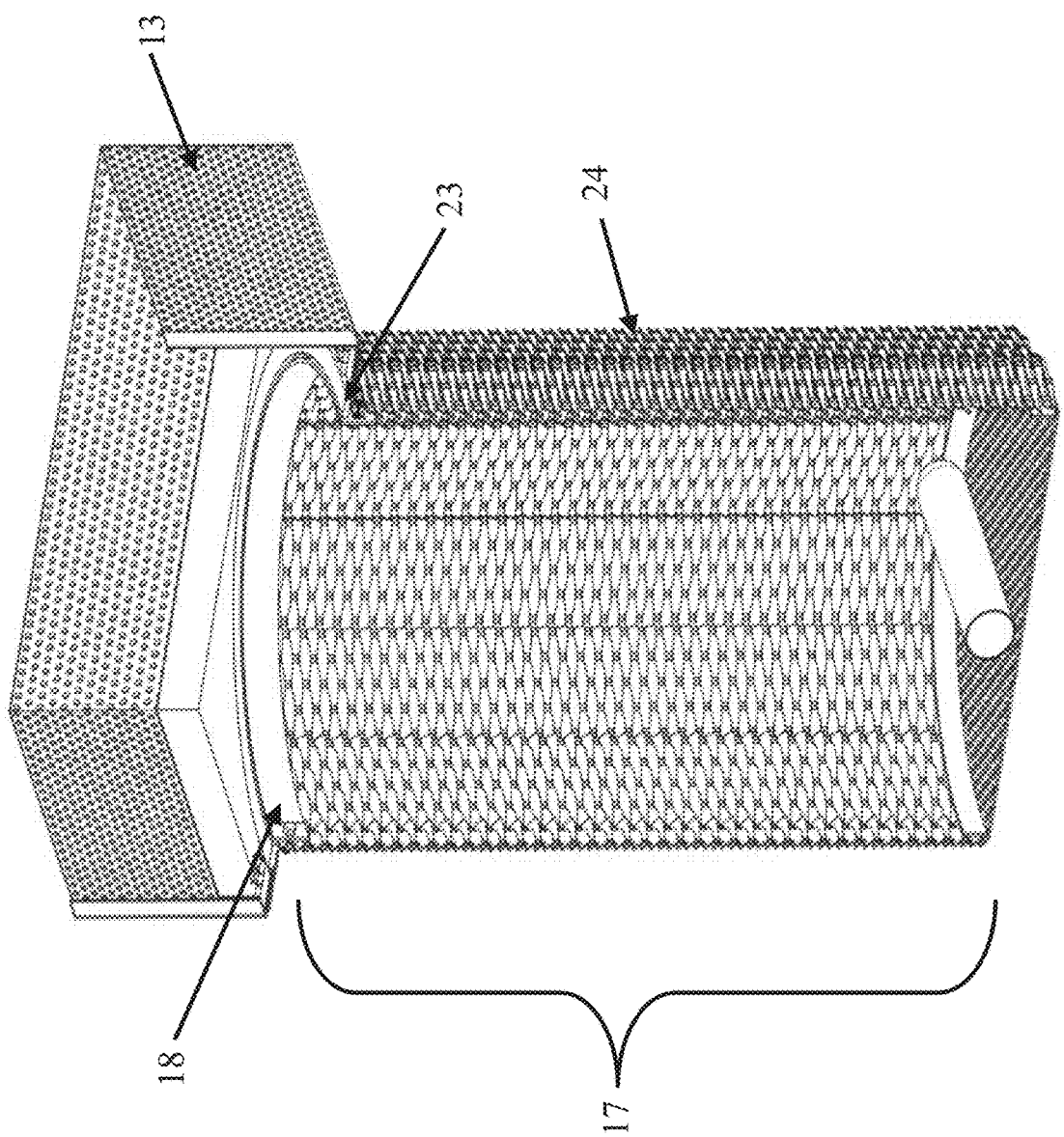

REMOVABLE TRASH FILTER BASKET WITH HINGED WIER FOR CATCH BASINS

CROSS-REFERENCE TO RELATED APPLICATIONS

The present application is a non-provisional application of U.S. Provisional Application No. 62/903,885 filed Sep. 20, 2019.

FIELD OF INVENTION

The embodiments of the present technology relate in general to an advanced catch basin filter system with a pivot weir for use in stormwater management treatment systems.

The pivot, or hinged weir is mounted to the weir which holds the filter basket and is designed to work in conjunction with many screens and filters but not limited to one or more full trash capture screens, multi-level screens, granular filter media, and membrane filters. Additional filtering devices for which the pivot weir may be applied include but is not limited to hydrocarbon booms, KRAKEN®, and other filter media.

One approach to treat stormwater known in the art is separation or sedimentation of materials that are not neutrally buoyant, as an example, particles that are heavier and trash and oils that are lighter. In the instant invention, the pivot weir controls the flow of water by reducing incoming velocities and maximizing flow of the flow path which allows trash, debris, total suspended solids (TSS), floatables, and oils to settle out of the stormwater and remain contained within the catch basin filter system for later removal. The combination of the diversion trough, weir, weir trash screen, and removable filter basket allow for full capture of trash and debris within stormwater or dry weather runoff and retention of trash and floatables during higher flow when the system is in bypass.

The backside of the weir hinge may be removed for more easy access to the catch basin. The pivot weir's function allowing for access to the filter screen from above ground without the additional steps of entering the catch basin is the only process known in the industry to the inventor at the time of this application filing. The removable filter basket and pivot weir allow for removal so that the catch basin and outlet pipe can be accessed by maintenance personnel for various requirement maintenance activities and cleaning.

The pivot weir position on the pivot weir may be adjusted for preferred fit and ease of use within a catch basin treatment system. In some embodiments the pivot weir is combined with an extension platform and affixed to the trough. Additional embodiments may include a wing connecting the trough and mounted above the pivot weir. Further, pivot weirs may accommodate different types of hinges, including but not limited to, piano hinges and top-pivoting pivot points.

In situations of high storm water flows, the pivot weir can be configured in the treatment system such that there is a bypass to move the water more quickly through the treatment system. The flow rate is then based upon the critical point of restriction, which is either the weir or the filter screen's capacities. Under high flow conditions, floatables are still retained within the treatment system.

The pivot weir in combination with a diversion trough is often comprised of stainless steel; however, other materials of similar engineering strength maybe substituted, including, but not limited to marine grade fiberglass, plastics and plastic molding.

BACKGROUND

Water treatment systems have been in existence for many years. These systems treat stormwater surface runoff or other polluted water. Stormwater surface runoff is of concern for two main reasons: one because of the effects of its volume and flow rate, and two, because of the pollution and contamination it can carry. The volume and flow rate of stormwater is important because high volumes and high flow rates can cause erosion and flooding. Pollution and contamination are important because stormwater is carried into our rivers and streams, from there into our lakes and wetlands, and furthermore because it can eventually reach our oceans. Pollution and contamination that is carried by stormwater can have adverse effects on the health and ecological balance of the environment.

In the early 2000s the EPA and California Regional Water Quality Boards issued what is known as a Total Maximum Daily Load for trash in the Los Angeles Region, specifically the Los Angeles River Watershed. Countless studies were done on the river and its discharge into the Pacific Ocean. It was found that the amount of trash entering the river basin from the storm water infrastructure far exceeded any acceptable levels. There were several environmental groups advocating for action to be taken to reduce the amount of trash discharged into the river and other watersheds.

More recently, efforts to prevent trash from entering municipal waterways further evolved in 2015 when the California Water Boards imposed a series of regulations and related site development permits for full trash capture requirements for stormwater treatment systems.

The Clean Water Act of 1972 enforced by the U.S. Environmental Protection Agency (EPA) set the stage for vast improvements to a water infrastructure and quality. Water pollution has been divided into two categories: point source and non-point source. Point sources include wastewater and industrial waste. Point sources are more easily identifiable, and therefore direct measures can be taken to control them. The other category, non-point source, is more difficult to identify. Stormwater runoff is the major contributor to non-point source pollution in rivers, lakes, streams and oceans. Studies have suggested and confirmed the leading cause of pollution to our waterways is from contaminated stormwater runoff. As we build houses, buildings, parking lots, roads and other impervious areas, we increase the amount of water that runs off the land and into our stormwater drainage systems, which all lead to rivers, lakes, streams and the ocean. As more land becomes impervious, less of the rain seeps back into the ground. This leads to less groundwater recharge and higher velocity flows in streams, which cause erosion and increased loads of contaminants into these waterways.

There are some sources of pollutants that are present in stormwater runoff. Sediments come from hillsides and other natural areas that are disturbed during construction and other human activities. When land is stripped of vegetation the soil more easily erodes and finds its way to storm drains. Trash and other unnatural debris are dropped on the ground every day which finds its ways into the drainage system and ultimately our waterways. Leaves from trees and grass clippings from landscape activities that land on hardscape areas no longer decompose back into the ground but flow to our storm drains and collect in huge concentrations in lakes and streams. These organic substances leach out huge loads of nutrients and they decompose and cause large algae blooms which deplete the dissolved oxygen levels and kill fish and other organisms. Other unnatural sources of nutrients including nitrogen, phosphorus, and ammonia come from residential and agricultural fertilizers that are used in access and find their way to storm drains. Nutrients are one of the number one pollutants of concern in our nations.

Other major pollutants of concern include heavy metals which come from numerous sources and are harmful to fish and other organisms including humans. Many of our waterways are no longer safe to swim in or fish in and therefore no longer have any beneficial use. Heavy metals include but are not limited to zinc, copper, lead, mercury, cadmium and selenium. These metals come from car tires and brake pads, paints, galvanized roofs and fences, industrial activities, minim, recycling centers, any metal materials left uncovered. Other major pollutants of concern are hydrocarbons which include oils and grease. These pollutants come from leaky cars and other heavy equipment and include hydraulic fluid, break fluid, diesel, gasoline, motor oils, cooking oils and other industrial activities.

Bacteria, pesticides and organic compounds are a few other categories of pollutants which are also harmful to our waterways, wildlife and humans. Over the last 20 years the EPA has been monitoring the pollutant concentrations in most of the streams, rivers and lakes throughout the country. Over 50% of four waterways are impaired for one or more of the above-mentioned pollutants. As part of the Phase 1 and Phase 2 NPDES (National Pollutant Discharge Elimination System) permits which control industrial and non-industrial development activities the control of these sources of pollutants in now mandated. Phase 1 was initiated in 1997 and Phase 2 was initiated in 2003. While there are many requirements to these permits the three main focuses are on source control, during construction pollution control and post construction pollution control. Post construction control mandates that any new land development or redevelopment activities are required to incorporate methods and solutions that both control increased flows of rain water off the site and decrease (filter out) the concentration of pollutants off of these developed sites. These are commonly known as quantity and quality control. Another part of these requirements is for existing publicly owned developed areas to retrofit the existing drainage infrastructure with quality and quantity control methods and technologies to decrease the existing amount of rainwater runoff and pollutant concentrations.

One of the main categories of technology that help with obtaining these goals are referred to as structural best management practices or BMPs. Structural BMPs are proprietary and non-proprietary technologies that are developed to store and/or remove pollutants from stormwater. Methods such as detention ponds, detention basins, or regional wetlands are used to control the volume of runoff which providing some pollutant reduction capabilities. Over the past 10 years numerous technologies have been invented to effectively store water underground and thus freeing up buildable land above them. Various treatment technologies such as catch basin filters, hydrodynamic separators, and media filters are used to remove pollutants. These technologies commonly work by using the following unit processes: screening, separation, physical filtration, and chemical filtration.

Additionally, stormwater is characterized by large concentrations of various pollutants including trash, debris and sediments. Reports have shown that for urbanized area an average of 7.6 cubic feet of trash and 2.4 cubic yards of sediment are generated per acre of impervious surface per year. In many areas, where proper erosion control measures are not taken, which is common, the loading of sediment is much higher. Therefore, a system which has a media bed designed to minimize clogging along with a pre-treatment chamber to remove trash and sediments provides huge advantages to the end user. Considering the collection of these pollutants, maintenance of stormwater BMPs can be very expensive and a burden to property owners. There is, thus a need for a system that can minimize maintenance costs.

A solution to address these problems which is well known in the art is to install catch basin filter cages. Examples of U.S. Pat. Nos. include 6,797,162 (Happel, H.); 7,186,333 (Kluge, R.); and 9,015,192 (Kent, G.).

While catch basin filters can be effective, they do not meet modern regulatory standards of full trash capture. Others do not engage filtering stages during high flow periods which leads to more trash and debris entering the local water channels. Some are difficult to maintain because the filter cages are difficult to access. The present invention solves for each of these limitations.

SUMMARY OF THE INVENTION

Certain embodiments of the invention provide systems that filter surface water runoff that enters sewer or storm drains. Some embodiments of such systems are comprised of a series of weirs designed to fully capture trash and debris. Components of storm drain filter systems of the present invention may be constructed from metal including marine grade stainless steel, fiberglass, plastic, concrete, or similar materials, or combinations thereof.

In some embodiments, the filter basket comprises two or more vertically tiered filters and is configured to channel surface water that has passed through the surface water intake opening of the top plate through the two or more filters, which can be made of perforated metal or wire mesh and operative to provide graduated filtration of particulate materials and large debris out of the surface water that flows therethrough.

In some embodiments, the filter comprises at least one layer of a solid state media or a granular media and is configured to channel surface water that has passed through the catch basin chamber through the at least one solid state or granular layer, which is operative to remove from the surface water that flows therethrough substantial amounts of suspended or dissolved fine sediments, pollutants, metals, nutrients, bacteria, or combinations thereof. In some embodiments, the surface water that flows through the enhanced media filter of a surface water filter system of the invention meets the United States National Pollutant Discharge Elimination Systems (NPDES) quality requirements.

In some embodiments, captured water moves through a diversion trough which provides complete coverage of an inlet. The diversion trough is designed to divert all flow to the filter and has full trash capture.

In some embodiments, the described invention may be inserted as a curb inlet filter or a grate inlet filter.

In some embodiments, a curb inlet filter can be a multi-level screening, Kraken®, and trash full capture in addition to embodiments utilizing media filters. In some embodiments, the filter basket can incorporate media filters with two or more filters in a vertically tiered arrangement, from bottom to top, of increasingly finer perforation or mesh, and wherein the vertically tiered arrangement is operative to provide a graduated filtration of particulate materials out of the surface water, and wherein the two or more filters are comprised of perforated metal, perforated plastic, perforated wood, wire mesh, plastic mesh, or combinations thereof.

In some embodiments, the trough includes a diverter which allows for continued trash capture even while creating a high water flow bypass. The diverter may be made of fiberglass or other suitable material.

In preferred embodiments, the trough is attached to a weir tray affixed atop of a filter basket. In some embodiments, the weir tray also contains a debris screen for further, initial filtration.

In preferred embodiments, the trough and weir tray combination are mounted against the catch basin wall directly below a manhole or other entrance to the catch basin for ease of removal and/or maintenance of the filter basket.

In preferred embodiments, includes a pivot, or hinge weir on top of the weir tray. Placement of the pivot weir provides optimal ease of access to the underlying filter basket.

In some embodiments, the filter basket can be cylindrical, square, or rectangular.

In some embodiments, the filter basket can be comprised of multi-level screen sizes to increase filtration.

In preferred embodiments, the filter basket screen includes holes no smaller than 4.7 mm in diameter which prevent clogging while still maintaining full capture standards.

In some embodiments, the filter basket can include a floating hydrocarbon boom or similar filter to capture smaller sized pollutants such as oils irrespective of the water level in the filter basket.

In some embodiments, multiple combinations of diversion trough, weir trays, and filter baskets can be mounted within a catch basin to increase treatment and storage capacity of a system.

In preferred embodiments, the diversion trough wall can be mounted at a lower level than the top of the wall of the hinged pivot weir and weir trash screen so during periods of high flow that exceed the capacity of the filter basket and weir trash screen the higher flows pass over the trough and not the weir.

In some embodiments, the instant invention can be installed upstream of an additional BMP system.

In some embodiments, the perimeter dimensions of a catch basin chamber filter unit exactly or substantially match the perimeter dimensions of a media filter unit in a surface water filter system of the invention.

In some embodiments, the top plate, the main catch basin chamber, and the media filter of a surface water filtration system of the invention are configured to allow for the main filter chamber and the enhanced filter chamber to be accessed, from a position above the surface water entry inlet and at a time that the filter system is mounted in a storm drain, for repair, maintenance, or replacement of the filters and media in the main chamber filtration and enhanced media filter units of the surface water filtration system.

In other embodiments, a metal louver is added to provide three dimensional openings which are oriented such that the opening facing the opposite direction of the flow path of stormwater prevents the clogging of openings.

In some embodiments, the perimeter dimensions of the catch basin chamber are equal to or less than perimeter dimensions of the enhanced media filter. In some embodiments, the storage reservoir comprises a drain. In some embodiments, the storage reservoir further comprises an overflow outlet pipe configured and operative to allow water to bypass the temporary storage reservoir when the storage reservoir is full.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings:

FIG. 10 is an iso view of an embodiment of the louver.

DETAILED DESCRIPTION OF PREFERRED EMBODIMENTS

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

Maintaining a regular schedule and paying maintenance fees stormwater systems can quickly become burdensome; therefore, it isn't uncommon for these systems to have a delay in maintenance. Delays in maintenance to remove captured trash and debris not only negates the well-intentioned regulatory guidelines instituted by municipalities; it can lead to local flooding because the catch basin is filled with debris and cannot store the same amount of water it was designed to store.

An additional issue with designs in the prior art is that as they become clogged with debris, particularly organic debris, if the catch basin filter isn't maintained on an as needed basis, the organic matter will begin to decay which can increase bacteria growth within the storm drain system, and could lead to increased attraction to the drain by vector insects, increasing a public health hazard and nuisance, and can also lead to localized odors wafting above ground.

A quick review of the prior art of catch basin filters can reveal the inherent issues present in the design as the filter baskets are enclosed and captured trash, debris, and pollutants must be manually removed in order to maintain the designed functionality of the filter basket and prevent flooding. This challenge is addressed in the instant invention through a combination of described elements, but particularly with the placement of the pivot or hinge weir.

A performance example of the pivot weir in combination with a multi-screen filter within a catch basin measured capture of mean particle sizes of 167 microns and as small as 75 microns. These results were verified by third party testing. The pivot weir treatment process can further be enhanced utilizing specific screening components that capture, isolate, and store larger debris and trash to increase overall system performance, create more laminar flow conditions, and prevent breakdown of trash, debris and organics such as leaves.

Figure 1:
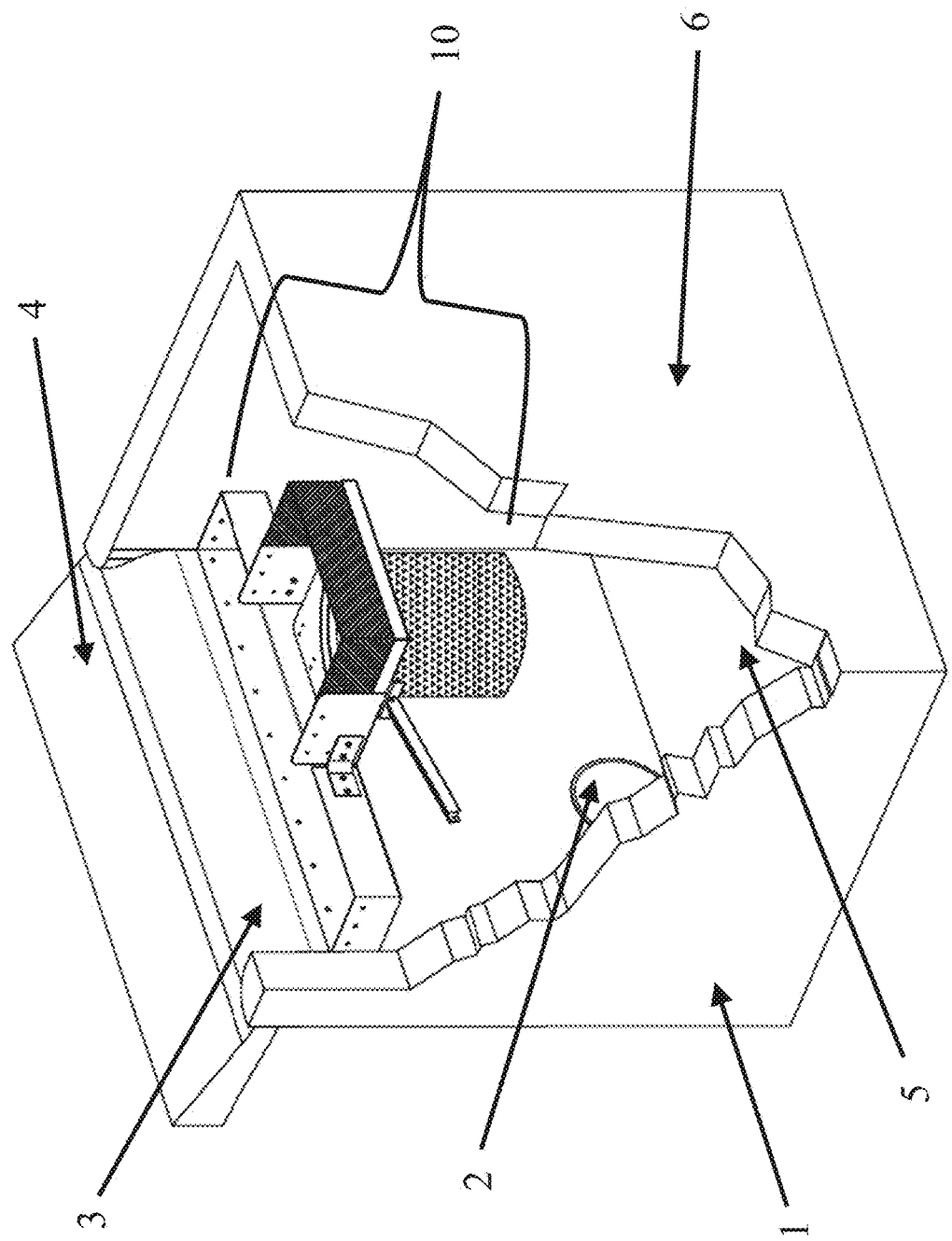
FIG. 1 is a cut-away view of an embodiment of the catch basin filter system with a pivot weir illustrating the overall system.

FIG. 1 begins to illustrate the overall catch basin with the catch basin filter assembly 10 within a catch basin 1. The assembly is in proximity of the curb and gutter 4 and the curb opening 3. The catch basin is also comprised of side walls 6 and a floor 5 and an outlet pipe 2.

Figure 2:
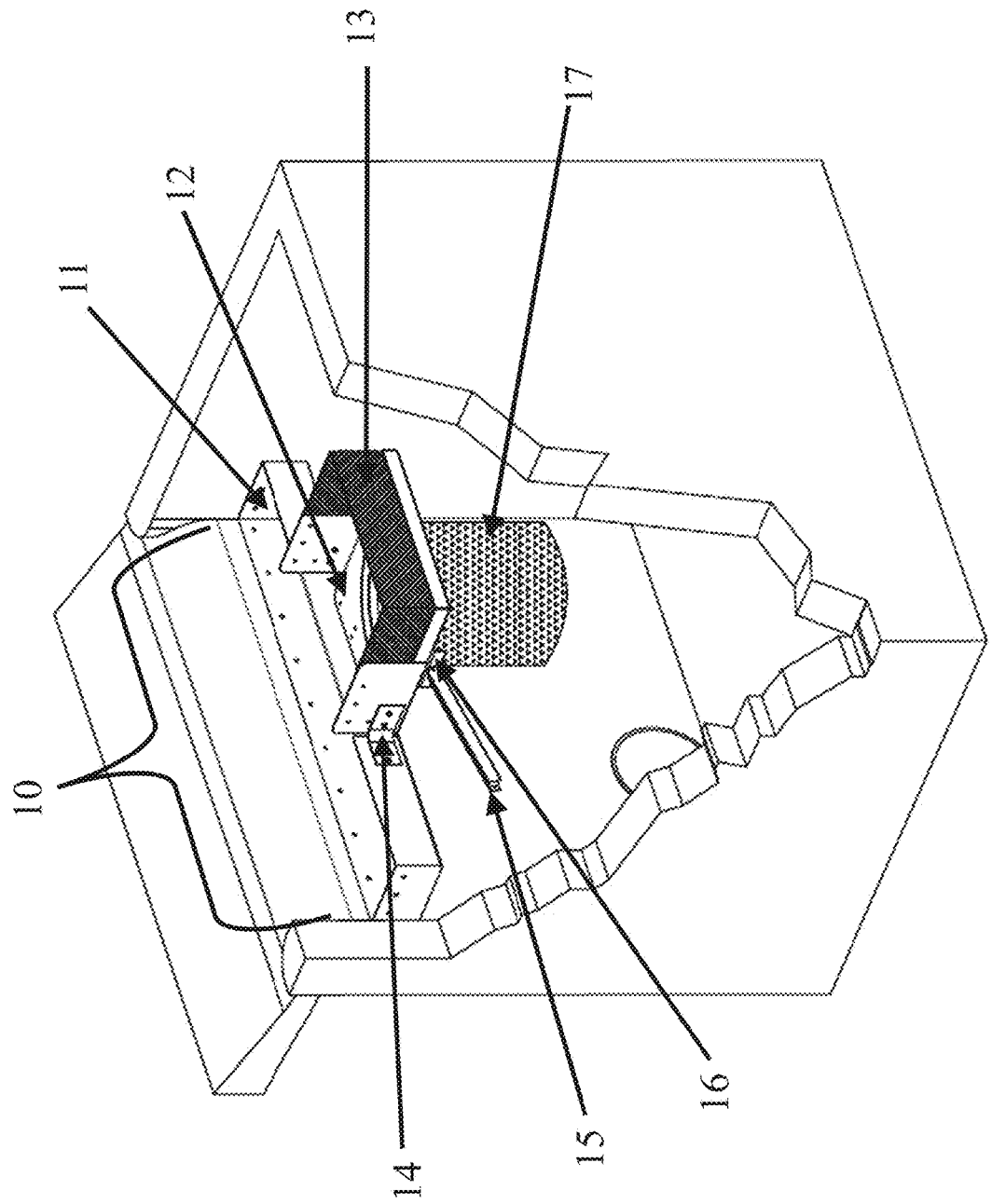
FIG. 2 is a cut-away view of an embodiment of the catch basin filter system with a pivot weir to emphasize the diversion trough with hinged pivot weir.

FIG. 2 provides a detailed view of the catch basin filter assembly 10, particularly illustrating the diversion trough 11, trough to weir mounting bracket 14, filter basked weir 12, undermounts 15, and trash filter basket 17.

Figure 3:
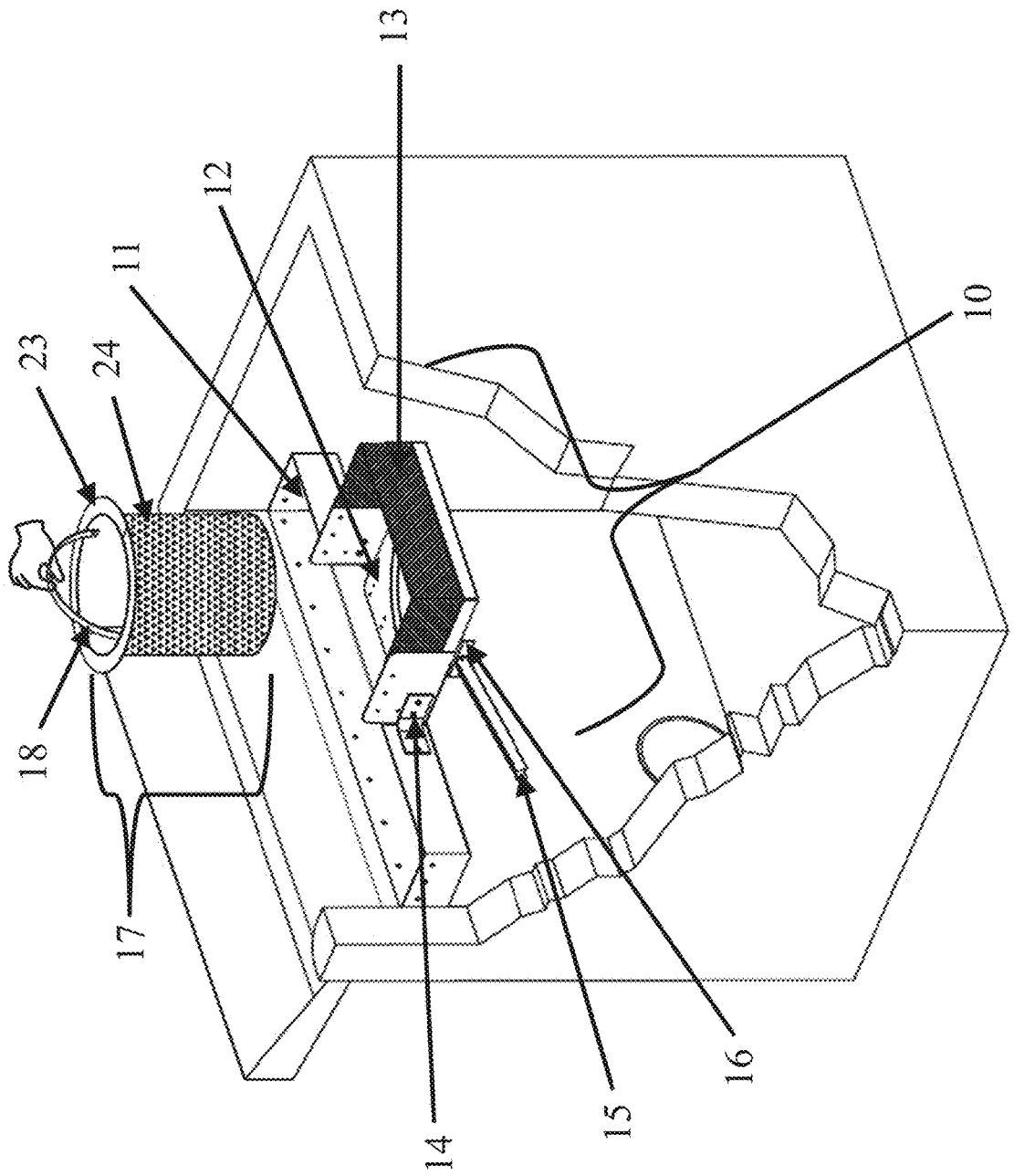
FIG. 3 is a cut-away view of an embodiment of the catch basin filter system with a pivot weir to emphasize the ease of filter basket removal.

FIG. 3 illustrates the ease of removal of filter basket 17 with a hinged handle 18 from the diversion trough 11, filter basket weir 12 and overall catch basin filter assembly 10. The assembly 10 is mounted via a trough to weir mounting brackets 14, undermounts 15, and also includes the weir stop 16.

Figure 4:
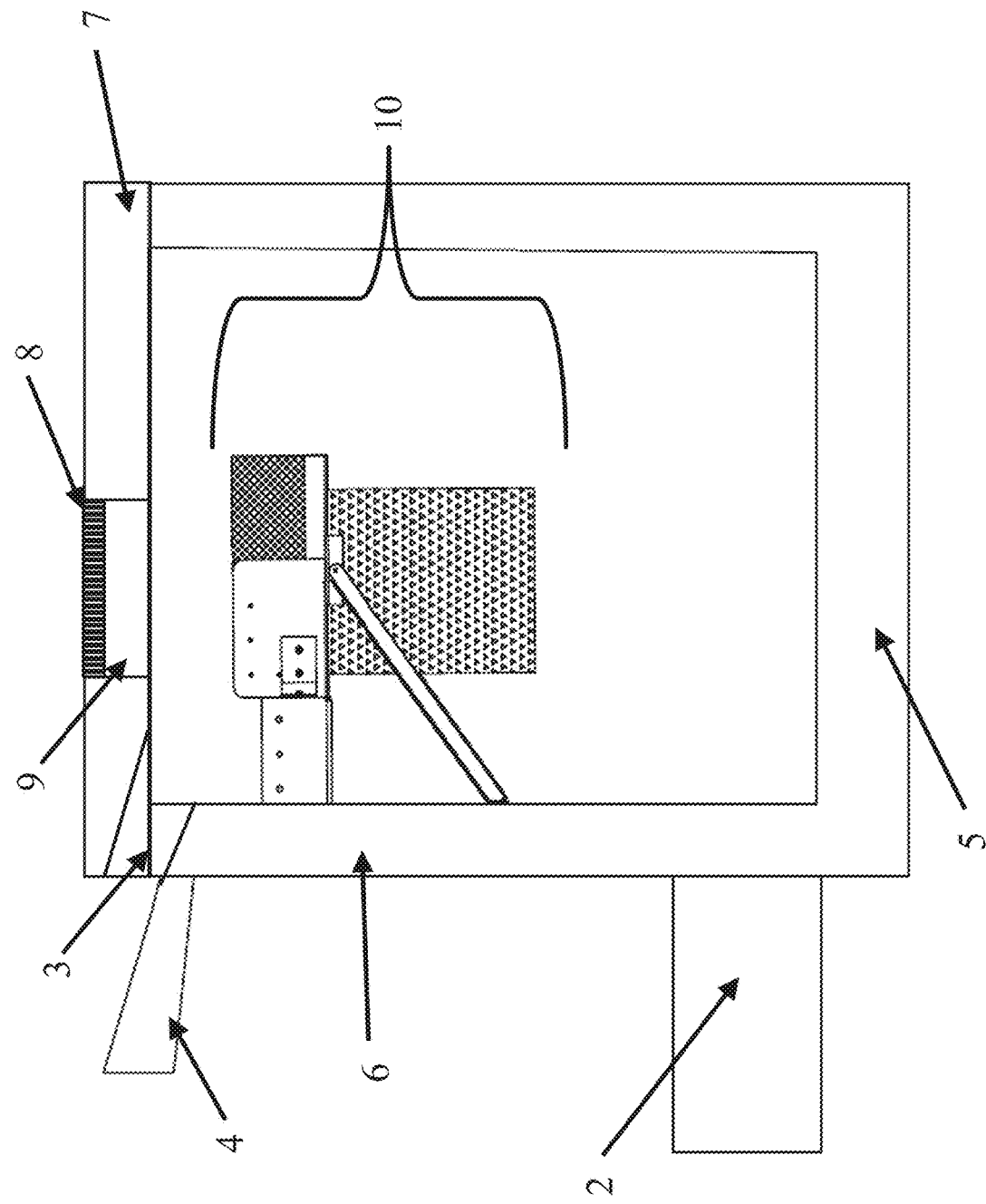
FIG. 4 is a side elevational section view of an embodiment of the catch basin filter system with a pivot weir illustrating the overall system.

FIG. 4 is a side view illustrating the catch basin filter assembly 10 installed within a catch basin 1 and the catch basin side wall 6 within position of the curb or gutter 4, a curb opening 3, manhole cover 8, catch basin access opening 9. The catch basin top 7, outlet pipe 2, and floor is also represented.

Figure 5:
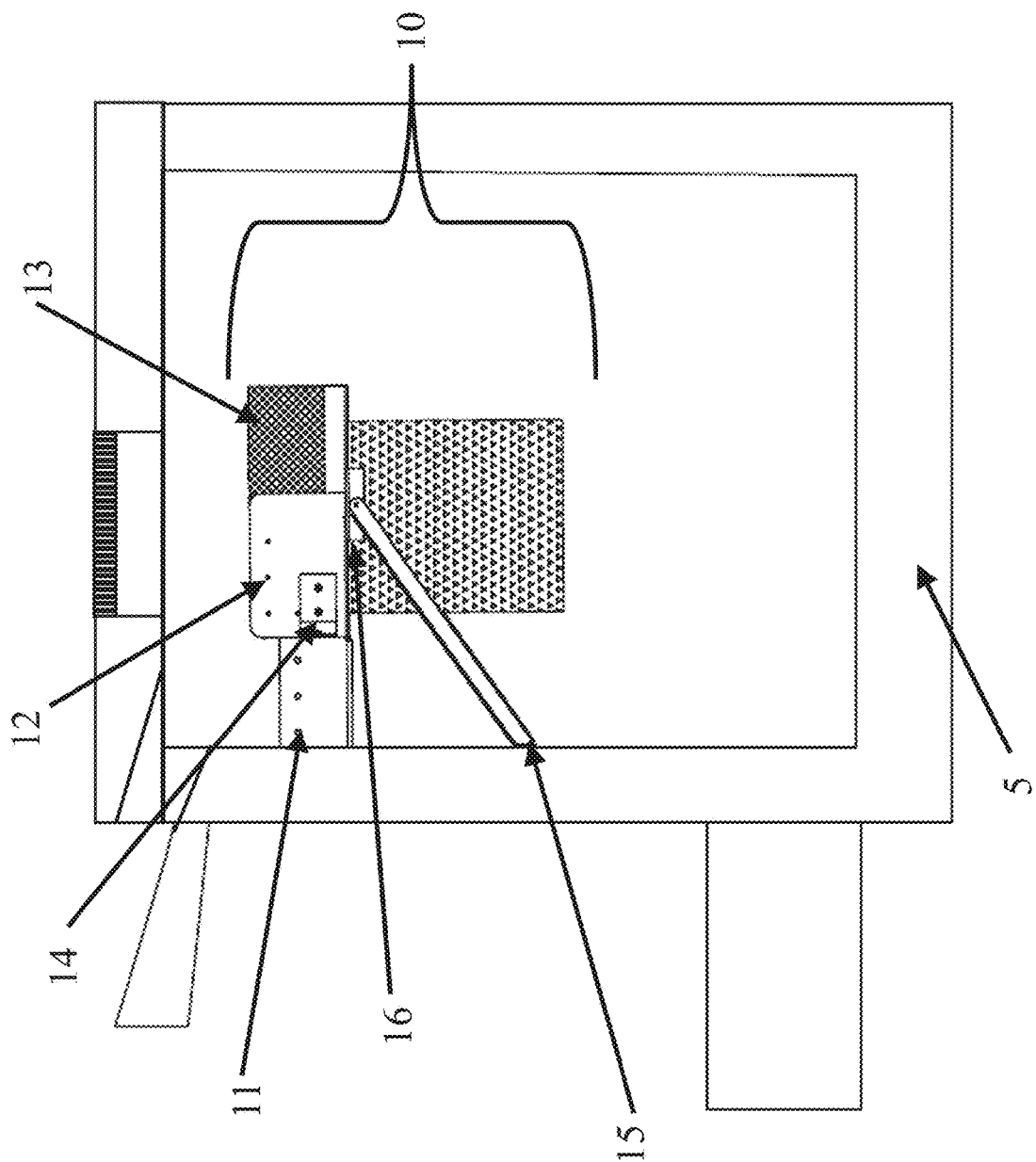
FIG. 5 is a side elevational section view of an embodiment of the catch basin filter system with a pivot weir particularly illustrating the mountings.

FIG. 5 illustrates an embodiment of the catch basin filter assembly 10, particularly highlighting the filter basket weir 12, a trough to weir mounting bracket 14, a side view of the diversion trough 11, a weir stop 16 and an undermount 15 to secure the trash and debris filter basket 17. The catch basin filter assembly 10 is above the catch basin floor 5.

Figure 6:
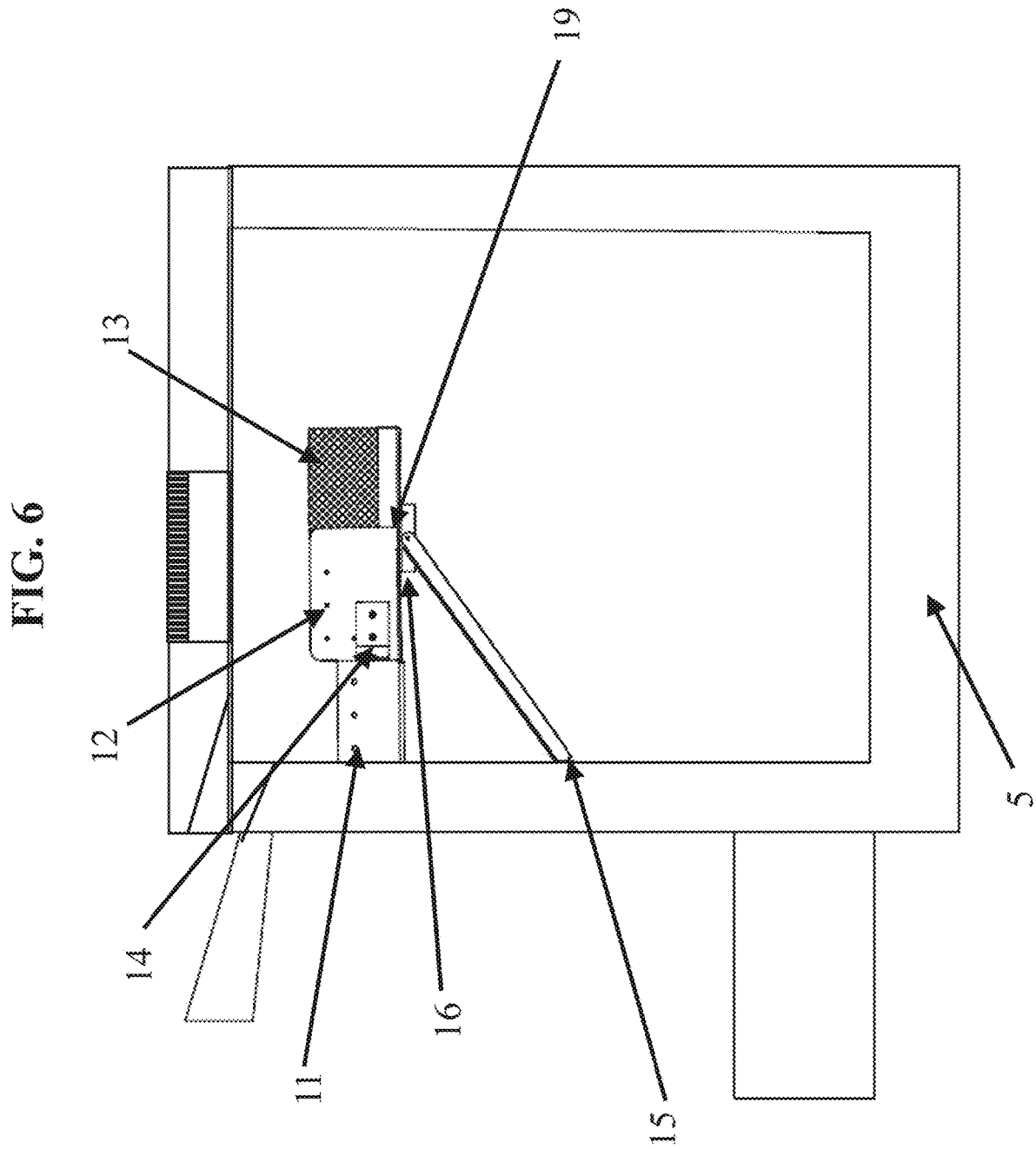
FIG. 6 is a top plan view of an embodiment of the catch basin filter system with a pivot weir.

FIG. 6 is another embodiment highlighting the hinge 19 between the weir debris screen 13, a diversion trough 11, the filter basket weir 12, a trough to weir mounting bracket 14, undermounts 15, and the catch basin floor 5.

Figure 7:
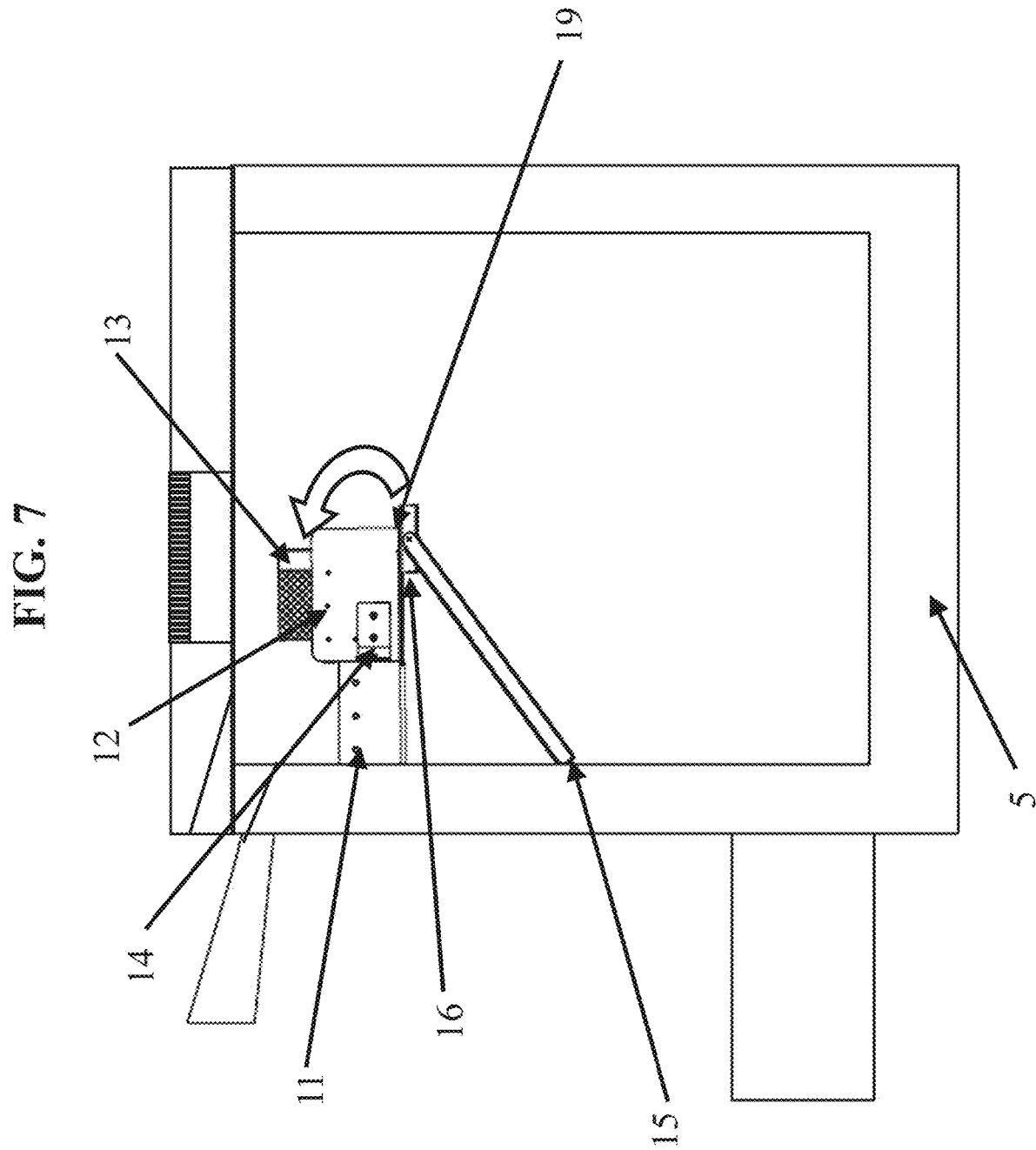
FIG. 7 is a top plan view of an embodiment of the catch basin filter system with a pivot weir in an open position.

FIG. 7 is an embodiment of the movement of the pivot hinge weir 13 over the filter basket weir 12 and a weir stop 16. In some embodiments, these can be adjusted to create a greater opening. The entire catch basin filter assembly 10 fits within a cutout 20. Also shown are the hinge between the weir 19, undermounts 15, a weir stop 16, the diversion trough 11, and the trough to weir mounting bracket 14.

Figure 8:
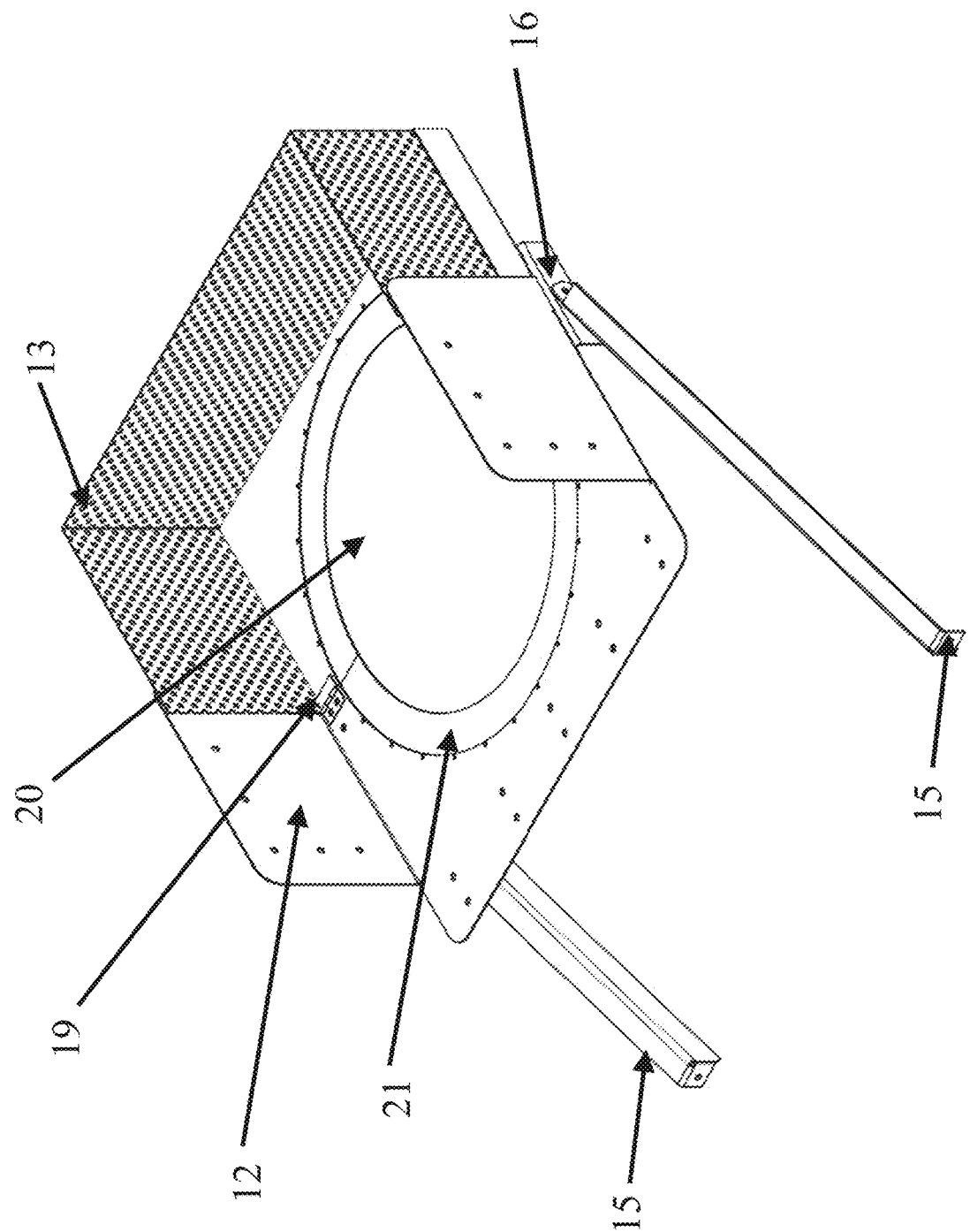
FIG. 8 is an iso view of an embodiment of the catch basin filter system with a pivot weir emphasizing the diversion trough system.

FIG. 8 provides a close up view of the weir cut out hole 20, with a recessed flange 21 wherein the trash filter basket 17 (not shown) rests inside the recessed flange 21. Also included is the hinged debris trash screen 13, the hinge between the weir and trash screen 19, the filter basket weir 12, a weir stop 16, and undermounts 15. Adjustments to the hinge can increase access to the catch basin filter assembly 10.

Figure 9:
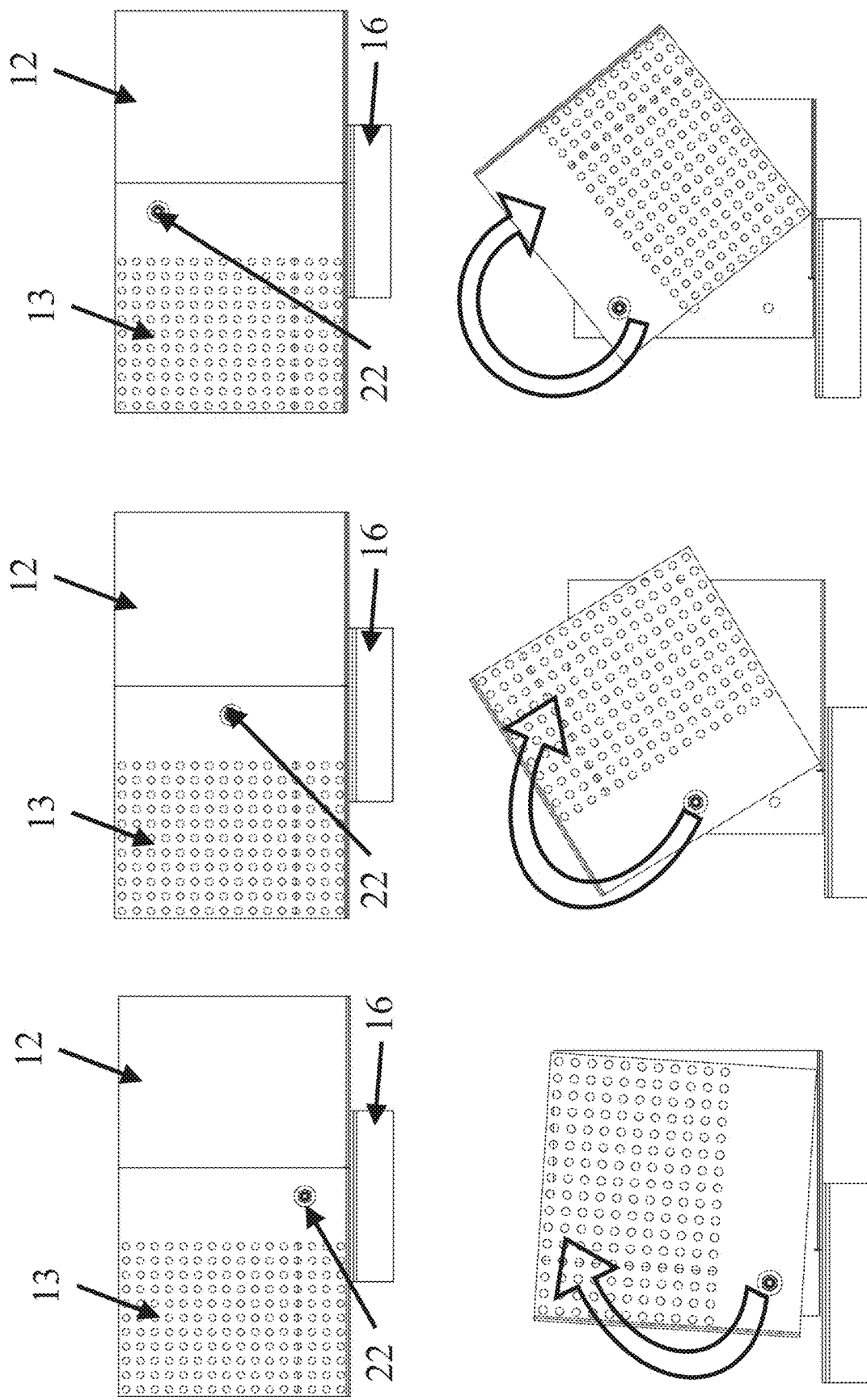
FIG. 9 is a top plan view of an embodiment of the catch basin filter system with the pivot weir in different orientations of opening.

FIG. 9 represents various positions of the pivot pin 22 within the debris screen weir 13 in association with the filter basket weir 12. In some embodiments, a bolt may be used to increase access. The pivot hinge debris screen weir 13 may open to at least 90 degrees depending on the placement of the pivot pin weir 22.

FIG. 10 represents the overall filter basket 17 with hinged handle 18 resting inside the recessed flange 23 and the louver 24 made of metal material. Also depicted is the pivot hinge debris screen weir 13.

The above description of disclosed embodiments is provided to enable any person skilled in the art to make or use the invention. Various modifications to the embodiments will be readily apparent to those skilled in the art, the generic principals defined herein can be applied to other embodiments without departing from spirit or scope of the invention. Thus, the invention is not intended to be limited to the embodiments shown herein but is to be accorded the widest scope consistent with the principals and novel features disclosed herein.

I claim:

1. A system, for filtering surface stormwater runoff inside a catch basin with a curb, grate, or combination opening that comprises a diversion trough, a bottom hinged pivot weir, weir to trough mounting brackets, under mounts, weir stops, a weir trash screen, a hole in the weir bottom section and a filter basket, wherein:

the diversion trough installed to the catch basin side wall below the curb, grate, or combination opening, running the entire width of the side wall until its ends intersect the two adjacent catch basin side walls to form a full gutter to intercept all incoming stormwater flows, the diversion trough attached to the side walls using mounting hardware;

the diversion trough having a side wall section opposite the catch basin side wall side cut out to attach and connect mechanically the bottom hinged pivot weir using weir to trough mounting brackets and mounting hardware;

the bottom hinged pivot weir extending horizontally from the diversion trough into the catch basin, said bottom hinged pivot weir with a bottom and two sides allow for stormwater runoff to enter from the diversion trough;

said bottom hinged pivot weir containing a three sided weir trash screen on its end opposite the diversion trough to retain trash and floatables during higher flow conditions;

said bottom hinged pivot weir containing a round hole cut out in its bottom to accept a filter basket, wherein the bottom hinged pivot weir contains two or more hinges in the bottom along the center line of the hole cut out;

wherein said filter basket can be easily removed from the weir cut out by lifting it upward from a filter basket folding handle, allowing the hinged pivot weir to fold upward 90 degrees or more, to allow for access into the catch basin below;

the filter basket with a top flange rests on the bottom hinged pivot weir bottom to allow stormwater runoff from the bottom hinged pivot weir to flow into it for further filtering of flow by the filtration mechanism before leaving the system into the bottom of the catch basin, the bottom hinged pivot weir further supported by under mounts attached to weir stops to provide structural support and said stops to prevent the bottom hinged pivot weir from bending when in operation;

said under mounts extending from the weir stops at an angle between 10 and 180 degrees and opposite ends attached to the side wall for additional support.

2. The system of claim 1, wherein the filter basket and weir trash screen are in a vertically tiered arrangement, from bottom to top, of increasingly finer perforation or mesh, and wherein the vertically tiered arrangement is operative to provide a graduated filtration of particulate materials out of the surface water, and wherein the two or more filters are comprised of perforated metal, perforated plastic, perforated wood, wire mesh, plastic mesh, or combinations thereof.

3. The system of claim 1, wherein the filter basket utilizes a louver expanded metal material with three dimensional openings that are oriented with said opening facing the opposite direction of the flow path to prevent clogging of openings.

4. The system of claim 1, wherein the hinged pivot weir is arranged at either the middle, either end of the diversion trough or at any space along its end.

5. The system of claim 1, wherein the top of the diversion trough wall is at a lower level than the top of the wall of the hinged pivot weir and weir trash screen so during periods of high flow that exceed the capacity of the filter basket and weir trash screen the higher flows pass over the trough and not the weir, therefore allowing trash and floatables in the weir to be retained.

6. A system, for filtering surface stormwater runoff inside a catch basin with a curb, grate, or combination opening that comprises a diversion trough, a side pin pivot weir, weir to trough mounting brackets, under mounts, weir stops, a weir trash screen, a hole in the weir bottom section and a filter basket, wherein:
   the diversion trough installed to the catch basin side wall below the curb, grate, or combination opening, running the entire width of the side wall until its ends intersect the two adjacent catch basin side walls to form a full gutter to intercept all incoming stormwater flows, the diversion trough attached to the side walls using mounting hardware;
   the diversion trough having a side wall section opposite the catch basin side wall side cut out to attach and connect mechanically the side pin pivot weir using weir to trough mounting brackets and mounting hardware;
   the side pin pivot weir extending horizontally from the diversion trough into the catch basin, said side pin pivot weir with a bottom and two sides allow for stormwater runoff to enter from the diversion trough;
   said side pin pivot weir containing a three sided weir trash screen on its end opposite the diversion trough to retain trash and floatables during higher flow conditions;
   said side pin pivot weir containing a round hole cut out in its bottom to accept a filter basket, wherein the side pin pivot weir contains two or more pins on the sides along the center line of the hole cut out;
   wherein said filter basket can be easily removed from the weir cut out by lifting it upward from a filter basket folding handle, allowing the side pin pivot weir to fold upward 90 degrees or more, to allow for access into the catch basin below;
   the filter basket with a top flange rests on the side pin pivot weir bottom to allow stormwater runoff from the side pin pivot weir to flow into it for further filtering of flow by the filtration mechanism before leaving the system into the bottom of the catch basin,
   the side pin pivot weir further supported by under mounts attached to weir stops to provide structural support and said stops to prevent the side pin pivot weir from bending when in operation;
   said under mounts extending from the weir stops at an angle between 10 and 180 degrees and opposite ends attached to the side wall for additional support.

7. The system of claim 6, wherein the filter basket and weir trash screen are in a vertically tiered arrangement, from bottom to top, of increasingly finer perforation or mesh, and wherein the vertically tiered arrangement is operative to provide a graduated filtration of particulate materials out of the surface water, and wherein the two or more filters are comprised of perforated metal, perforated plastic, perforated wood, wire mesh, plastic mesh, or combinations thereof.

8. The system of claim 6, wherein the filter basket utilizes a louver expanded metal material with three dimensional openings that are oriented with said opening facing the opposite direction of the flow path to prevent clogging of openings.

9. The system of claim 6, wherein the hinged pivot weir is arranged at either the middle, either end of the diversion trough or at any space along its end.

10. The system of claim 6, wherein the top of the diversion trough wall is at a lower level than the top of the wall of the hinged pivot weir and weir trash screen so during periods of high flow that exceed the capacity of the filter basket and weir trash screen the higher flows pass over the trough and not the weir, therefore allowing trash and floatables in the weir to be retained.

11. The system of claim 6, wherein the side pin pivot weir is located near the bottom portion of the sidewall.

12. The system of claim 6, wherein the side pin pivot weir is located near the center portion of the sidewall.

13. The system of claim 6, wherein the side pin pivot weir is located near the top portion of the sidewall.

* * * * *